(12) United States Patent
Grodzki

(10) Patent No.: US 10,204,426 B2
(45) Date of Patent: Feb. 12, 2019

(54) PREPARATION OF A SCAN PROTOCOL OF A MEDICAL IMAGING APPARATUS

(71) Applicant: David Grodzki, Erlangen (DE)

(72) Inventor: David Grodzki, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 15/218,023

(22) Filed: Jul. 23, 2016

(65) Prior Publication Data

US 2017/0024911 A1   Jan. 26, 2017

(30) Foreign Application Priority Data

Jul. 23, 2015 (DE) .................. 10 2015 213 910

(51) Int. Cl.
    *G06T 11/00*    (2006.01)
    *A61B 5/055*    (2006.01)
    *G01R 33/20*    (2006.01)

(52) U.S. Cl.
    CPC ............ *G06T 11/005* (2013.01); *A61B 5/055* (2013.01); *G01R 33/20* (2013.01)

(58) Field of Classification Search
    USPC ........................................ 382/128, 131–132
    See application file for complete search history.

(56) References Cited

U.S. PATENT DOCUMENTS

| | | | |
|---|---|---|---|
| 7,051,286 B1 | 5/2006 | Stemmer et al. | |
| 8,604,786 B2* | 12/2013 | Stemmer | A61B 5/055 324/307 |
| 8,755,574 B2* | 6/2014 | Declerck | A61B 6/037 382/128 |
| 9,078,566 B2* | 7/2015 | Profio | A61B 6/03 |
| 9,317,580 B2* | 4/2016 | Cohen-Solal | G06F 17/30598 |
| 9,523,750 B2* | 12/2016 | Senegas | G01R 33/543 |
| 2003/0144589 A1 | 7/2003 | Roell | |

(Continued)

FOREIGN PATENT DOCUMENTS

| | | |
|---|---|---|
| CN | 1422594 A | 6/2003 |
| DE | 102009054990 A1 | 6/2011 |

OTHER PUBLICATIONS

German Office Action for German Application No. 10 2015 213 910.7, dated Mar. 25, 2016, with English Translation.

(Continued)

*Primary Examiner* — Ishrat I Sherali
(74) *Attorney, Agent, or Firm* — Lempia Summerfield Katz LLC

(57) ABSTRACT

Preparation of a scan protocol of a medical imaging apparatus is provided. A first parameter set that includes one or more first scan parameters is provided. One or more first scan parameter values that are assigned to the one or more first scan parameters are set. Based on these set one or more first scan parameter values, a second parameter set that includes one or more second scan parameters is determined. The second parameter set is provided, and one or more second scan parameter values that are assigned to the one or more second scan parameters are set. Based on the one or more first scan parameter values and/or the one or more second scan parameter values, a scan protocol is prepared. Based on the scan protocol prepared, scan data is acquired by the medical imaging apparatus.

17 Claims, 4 Drawing Sheets

(56) References Cited

U.S. PATENT DOCUMENTS

| | | | |
|---|---|---|---|
| 2005/0154292 A1* | 7/2005 | Tank | A61B 5/055 |
| | | | 600/410 |
| 2007/0165930 A1* | 7/2007 | Feuerlein | G06T 1/60 |
| | | | 382/128 |
| 2011/0153255 A1 | 6/2011 | Horger et al. | |
| 2011/0228998 A1* | 9/2011 | Vaidya | G01R 33/543 |
| | | | 382/131 |

OTHER PUBLICATIONS

Chinese Office Action for Chinese Application No. 201610525942.0 dated Nov. 2, 2018, with English Translation.

* cited by examiner

PREPARATION OF A SCAN PROTOCOL OF A MEDICAL IMAGING APPARATUS

This application claims the benefit of DE 10 2015 213 910.7, filed on Jul. 23, 2015, which is hereby incorporated by reference in its entirety.

BACKGROUND

The present embodiments relate to preparation of a scan protocol of a medical imaging apparatus.

Imaging methods are important aids in medical technology. For example, in clinical sectional imaging, magnetic resonance tomography (MRT) is distinguished by high and variable soft tissue contrast levels. Depending on scan parameters such as echo time, repetition time, prepulses, and sequence types, the most diverse contrasts, such as T1 or T2-weighting or susceptibility weighting, may be set. In addition, the image field, resolution, and slice thickness may be set. Also in other modalities, particular setting values (e.g., tube current and tube voltage in computed tomography (CT)) influence the quality of the resulting images. The complete set of parameter settings is known as the scan protocol.

The setting of scan parameters of a scan protocol is carried out by an existing scan protocol being provided to a user, for example, by the user opening a scan protocol file on a control unit. The user receives direct access to all the adjustable scan parameters. The user may then change the values of the scan parameters (e.g., the scan parameter values in any desired sequence) and as often as desired. After changing one of the scan parameter values, any scan parameter values that are dependent on the changed scan parameter values are calculated anew and presented. Due to the complexity of the parameterization, this often leads to results that are confusing to the user.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method that facilitates the creation of a scan protocol is provided.

The method for the preparation of a scan protocol of a medical imaging apparatus includes providing a first parameter set that includes one or more first scan parameters. One or more first scan parameter values that are assigned to the one or more first scan parameters are set. Based on these set one or more first scan parameter values, a second parameter set that includes one or more second scan parameters is determined. The second parameter set is provided, and one or more second scan parameter values that are assigned to the one or more second scan parameters are set. Based on the one or more first scan parameter values and/or the one or more second scan parameter values, a scan protocol is prepared. The preparation of the scan protocol may take place both based on the plurality of first scan parameter values and also the one or more second scan parameter values. Based on the scan protocol prepared, scan data is acquired by the imaging examination apparatus.

The provision of the parameter sets (e.g., the first and second parameter sets) may take place, for example, using a display unit that includes, for example, a screen. The setting of the scan parameter values (e.g., the first and second scan parameter values) may take place, for example, using an input unit that includes, for example, a keyboard and/or a computer mouse. The determination of parameter sets (e.g., the second parameter set) may take place, for example, using an evaluation unit that may include, for example, processors. The display unit and/or the input unit and/or the evaluation unit may be included by a medical imaging apparatus.

A method includes at least two data input acts (e.g., an act for setting one or more first scan parameter values and an act for setting one or more second scan parameter values, where in the respective at least two data input acts, different subsets of the overall adjustable scan parameters may be set and/or changed). Following the parameter settings in the first data input act, calculations may be made for the parameter ranges available in the second data input act.

Using the proposed method, the most simple and intuitive possible operation of the medical imaging apparatus may be achieved. For example, the potential user may be protected against confusing scan parameter changes.

In one embodiment, the second parameter set includes a parameter space that is restricted by the already set one or more scan parameter values (e.g., by the one or more first scan value parameters). For example, the sequence in which the provision of the parameter sets with scan value parameters that may be set in the data input acts takes place is selected so that the possible parameter space is restricted further from step to step. In one embodiment, the scan value parameters with the greatest influence on other scan value parameters are requested, where possible, in the first data input act (e.g., these scan value parameters are included in the first parameter set, whereas scan value parameters with no influence on other scan value parameters are requested in subsequent data input acts, such as in the last data input act). By this, the number of the necessary data input acts and/or the number of the adjustable scan parameters may be minimized so that the preparation of the scan protocol of the medical imaging apparatus may be performed quicker and easier.

For example, the method may be configured so that on setting of the one or more second scan parameter values, a part of the already set one or more scan parameter values is not changeable. By this, the potential user is led efficiently through the preparation process of the scan protocol, and the risk of possible faulty inputs may be reduced.

According to a further embodiment, the method includes one or more additional method portions, where each of the one or more additional method portions includes: based on previously set scan parameter values such as, for example, the at least one first scan parameter value and/or the at least one second scan parameter value and/or any other further scan parameter values, a further parameter set that includes one or more further scan parameters is determined. This further parameter set is provided, and one or more further scan parameter values are set. The further scan parameter values are assigned to the one or more further scan parameters. The preparation of the scan protocol is carried out based on the additional one or more further scan parameter values that have been set in the one or more additional method portions (e.g., apart from the one or more first scan parameter values and/or the one or more second scan parameter values, the one or more further scan parameter values are now additionally used for preparing the scan protocol).

Thus, apart from the first two data input acts in which the one or more first scan parameter values and the one or more second scan parameter values are set, the method may include further data input acts. In this way, the preparation of more complex scan protocols where, for example, the scan parameters have multiple dependency may also be performed.

The further parameter set may also include a parameter space that is restricted by the scan parameter values already set (e.g., by the one or more first scan parameter values and/or the one or more second scan parameter values and/or any other further scan parameter values).

In one embodiment, in such cases, on setting the at least one further scan parameter value, a part of the already set scan parameter values (e.g., the one or more first scan parameter values and/or the one or more second scan parameter values and/or any other scan parameter values) is not changeable.

In addition, during the provision of the parameter sets (e.g., during the provision of the first and/or second and/or any further parameter set), at least partially pre-determined scan parameter values (e.g., default values) are suggested. The default values may have been set before the start of the method, but the default values may also be calculated during the determination of a parameter set, taking account of previously set scan parameter values and/or taking account of device-specific conditions of the medical imaging apparatus. This simplifies an optimum exploitation of the efficiency of the medical imaging apparatus. In addition, on setting of the one or more scan parameter values, no scan parameter value may be changed, and the preparation of the scan protocol and the acquisition of the scan data may be started directly.

In one embodiment, on determining a parameter data set (e.g., the first and/or second and/or some further parameter set) for at least one of the scan parameters of the parameter set, a permissible value range that restricts the setting of the scan parameter value of the at least one scan parameter is determined. In this way, the optimal use of the efficiency is simplified, since the possible value range for a scan parameter may be displayed to the user on provision of the parameter set. For example, a setting (e.g., a value input) outside the determined value range may be directly prevented, for example, by a false input into an input screen being displayed and/or a Next button being deactivated.

An embodiment of the method includes additional acts. At least one postprocessing parameter is provided, and at least one postprocessing parameter value that is assigned to the at least one postprocessing parameter is set. Postprocessing parameters typically serve to influence any postprocessing and/or preparation of the scan data recorded and may concern, for example, filters, etc.

It may be provided for an item of status information to be prepared that is dependent on a number of scan parameter values that are still to be set and/or on a number of parameter sets that include the scan parameter values that are still to be set. A progress bar may be displayed to the possible user, which indicates how far the preparation has progressed and/or displays a number of subsequent data input acts. By this, the possible user receives an improved orientation within the input process.

In one embodiment, the imaging examination apparatus includes a magnetic resonance tomograph and/or a computed tomography unit and/or an X-ray system since, due to the highly complex scan protocols with which such devices are typically operated, the proposed multi-step parameterization method may be particularly advantageously used.

Advantageously, using the scan parameter values set, a slice orientation and/or a slice position and/or a slice thickness and/or a slice count and/or a slice separation and/or a matrix size and/or a field of view and/or a selection of acquisition coils and/or an echo time and/or a repetition time and/or an inversion time and/or a slice linkage and/or a bandwidth and/or a turbo factor and/or a direction of the phase encoding and/or an averaging are set.

One embodiment provides that in at least one additional monitoring act, the scan parameter values set are checked for adherence to at least one boundary condition.

For example, the at least one boundary condition may take account of technical limitations of the medical imaging apparatus and/or safety considerations. It may thus be achieved that the acquisition of the scan data may take place safely and reliably. For example, thereby, an optimum use of the efficiency of the medical imaging apparatus (e.g., a gradient system and/or a high frequency system of a magnetic resonance tomograph) may be facilitated.

For example, the at least one boundary condition may include a maximum stimulation and/or a maximum heating and/or a maximum high frequency exposure. These are particularly important safety aspects during operation of magnetic resonance tomographs.

In one embodiment, on non-compliance with the at least one boundary condition, in a further act, at least one of the previously set scan parameter values is set again (e.g., if the scan parameter values have been set so that one or more boundary conditions are not met, then the relevant scan parameter values may be amended in a further act).

In one embodiment, on repeated setting of previously set scan parameter values, at least one of the scan parameter values to be set again is suggested. The determination of the suggestion may take place based on the previously set scan parameter values. This facilitates protocol setting for the possible user.

In addition, a medical imaging apparatus that is configured to carry out a method for preparation of a scan protocol of a medical imaging apparatus is provided. The medical imaging apparatus includes a display unit for provision of a plurality of parameter sets, each including at least one scan parameter, an input unit for setting the scan parameters, and an evaluation unit for determining a parameter set based on the at least one scan parameter value that has been set.

The advantages of the medical imaging apparatus according to one or more of the present embodiments substantially match the advantages of the method for preparation of a scan protocol of a medical imaging apparatus, as described in detail above. Features, advantages, or alternative embodiments mentioned therein may also be transferred to the other descriptions and vice versa.

In other words, the present description may also be further developed with the features disclosed in conjunction with a method. The corresponding functional features of the method are herein configured by suitable modules as contained herein (e.g., hardware modules).

In addition, a computer program product that includes a program and is directly loadable into a memory store of a programmable computer unit of a medical imaging apparatus and includes program instructions in order to carry out a method for the preparation of a scan protocol of a medical imaging apparatus when the program is executed in the computer unit of the medical imaging apparatus is provided.

The computer program product may herein include an item of software with a source code that is to still be compiled and linked or is to be interpreted, or an executable software code that, for execution, is only to be loaded into the memory store of the computer unit of the medical imaging apparatus. By the computer program product, the method according to one or more of the present embodiments may be carried out rapidly, exactly reproducibly and robustly. The computer program product is configured such that the computer program product is able to carry out the method acts according to one or more of the present embodiments by the computer unit. The computer unit is to have the respective pre-conditions such as, for example, a suitable working memory store, a suitable graphics card, or a suitable logic unit so that the respective method acts may be carried out efficiently. The computer program product is stored, for example, on a computer-readable medium or is deposited on a network or server from where the computer program product may be loaded into a processor of the system control unit. Examples of computer-readable media are a DVD, a magnetic tape, or a USB stick, on which electronically readable control information (e.g., software) is stored. One or more of the present embodiments may therefore also proceed from the aforementioned computer-readable medium.

BRIEF DESCRIPTION OF THE DRAWINGS

Parts that correspond to one another are provided with the same reference signs in all the drawings.

DETAILED DESCRIPTION

Figure 1:
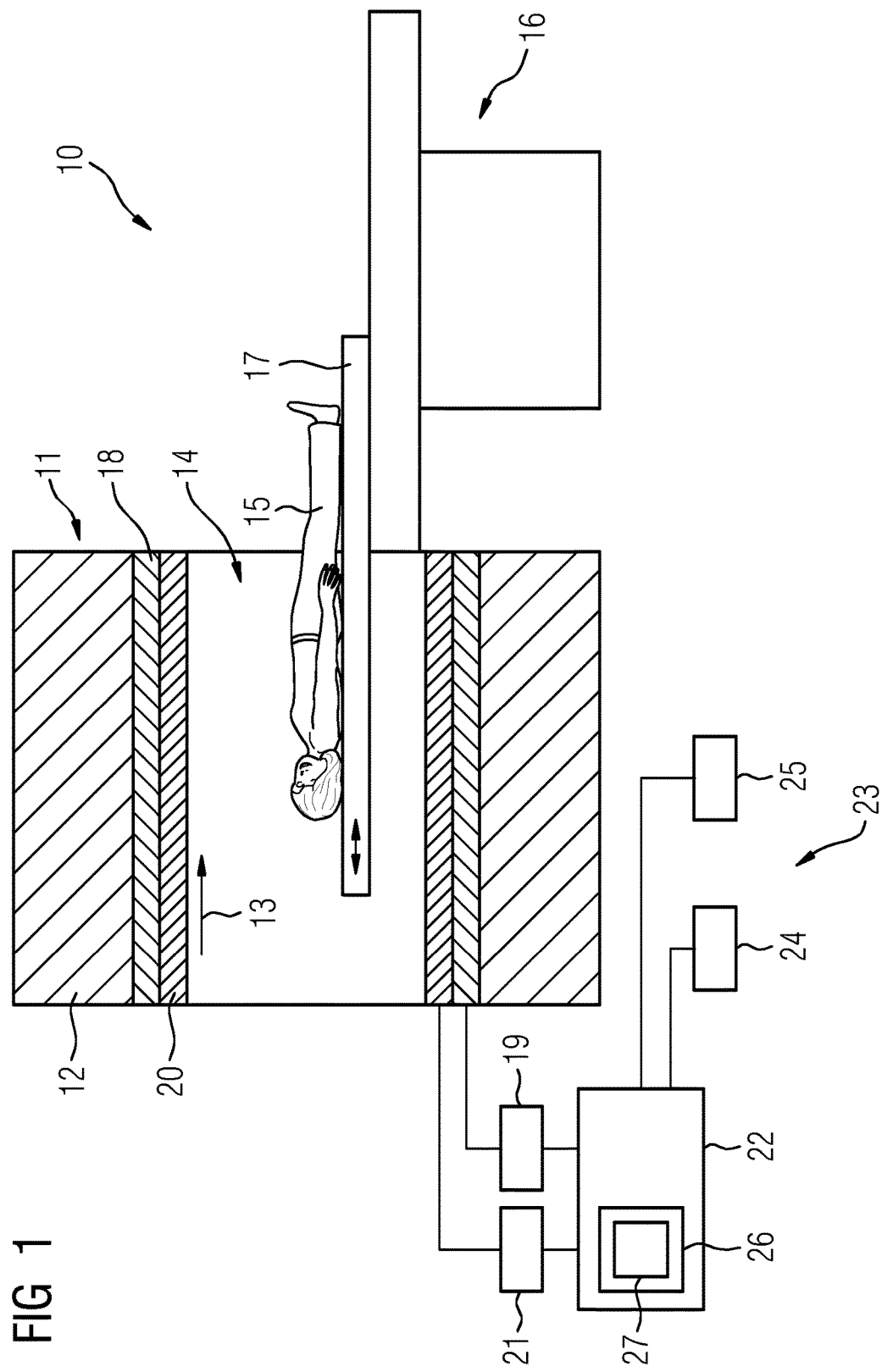
FIG. 1 is a representation of a magnetic resonance tomograph as an example of a medical imaging apparatus.

FIG. 1 shows schematically a magnetic resonance tomograph 10 as an example of a medical imaging apparatus according to one or more of the present embodiments. The magnetic resonance tomograph 10 includes a magnet unit 11 that has a superconducting main magnet 12 for generating a strong and, for example, temporally constant main magnetic field 13. In addition, the magnetic resonance tomograph 10 includes a patient accommodating region 14 to accommodate a patient 15. In the present exemplary embodiment, the patient accommodating region 14 may be cylindrical and is surrounded cylindrically in a peripheral direction by the magnet unit 11. A configuration of the patient accommodating region 14 deviating therefrom may also be provided. The patient 15 may be pushed by a patient positioning apparatus 16 of the magnetic resonance tomograph 10 into the patient accommodating region 14. For this purpose, the patient positioning apparatus 16 includes a patient table 17 that is configured to be movable within the patient accommodating region 14.

The magnet unit 11 also includes a gradient coil unit 18 for generating magnetic field gradients that are used for position encoding during imaging. The gradient coil unit 18 is controlled by a gradient control unit 19 of the magnetic resonance tomograph 10. The magnet unit 11 further includes a high frequency antenna unit 20 that is configured in the present exemplary embodiment as a body coil that is firmly integrated into the magnetic resonance tomograph 10. The high frequency antenna unit 20 is configured to excite atomic nuclei in the main magnetic field 13 generated by the main magnet 12. The high frequency antenna unit 20 is controlled by a high frequency antenna control unit 21 of the magnetic resonance tomograph 10 and radiates HF magnetic resonance sequences into an examination space that is substantially formed by a patient accommodating region 14 of the magnetic resonance tomograph 10. The high frequency antenna unit 20 is also configured for the reception of magnetic resonance signals.

For controlling the main magnet 12, the gradient control unit 19 and for controlling the high frequency antenna control unit 21, the magnetic resonance tomograph 10 include a system control unit 22. The system control unit 22 centrally controls the magnetic resonance tomograph 10 (e.g., the execution of a pre-determined imaging gradient echo sequence based on a scan protocol). For example, the system control unit 22 includes a programmable computer unit 26 that includes a memory store (e.g., a non-transitory computer-readable storage medium; not shown in detail here) into which a computer program product is loadable. The computer program product includes program instructions in order to carry out a method for preparation of a scan protocol when the program is executed in the computer unit of the medical imaging apparatus.

In order to carry out this method, the computer unit 26 also includes an evaluation unit 27 that may include, for example, processors for determining a parameter set based on scan parameter values that may be input via a user interface 23 that is connected to the system control unit 22. For example, the user interface 23 includes a display unit 24 for the provision of a plurality of parameter sets that each include at least one scan parameter, and an input unit 25 for setting the scan parameter values. For this purpose, the display unit 24 may include, for example, one or more monitors, and the input unit 25 may include a keyboard and/or a computer mouse.

The magnetic resonance tomograph 10 disclosed in the present exemplary embodiment may include further components that magnetic resonance tomographs typically have. A general mode of operation of a magnetic resonance tomograph 10 is also known to a person skilled in the art, so that a detailed description of the general components is omitted.

Figure 2:
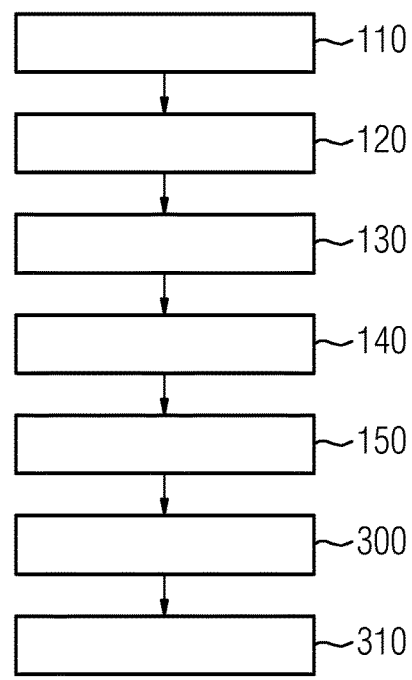
FIG. 2 is a block diagram of one embodiment of a method.

FIG. 2 shows a block diagram of a method according to one or more of the present embodiments for the preparation of a scan protocol of a medical imaging apparatus. In act 110, a first parameter set that includes one or more first scan parameters is provided to an operator of the magnetic resonance tomograph 10 by the display unit 24. For example, this parameter set includes only scan parameters that identify an orientation and/or a rotation and possibly also a field of view and a slice coverage of an acquisition to be carried out. Any further scan parameters may be suppressed and/or not displayed.

For example, through input via the input unit 25, in act 120, the operator may set one or more first scan parameter values that are assigned to the one or more first scan parameters. Once this is completed, the operator may click, for example, on a Next button.

Based on the one or more first scan parameter values, the evaluation unit 27 then determines in act 130 a second parameter set that includes one or more second scan parameters. In the example shown, for example, depending on the selected rotation, a maximum possible gradient strength for operating the gradient coil unit 18 and/or a maximum high frequency power for operating the high frequency antenna unit 20 may be calculated. Following therefrom, the scan parameter values adjustable in this regard during the further process may be determined.

From this, there follows a second parameter set that may be provided (e.g., displayed) to the user via the display unit 24 in act 140. Here, for example, all or a selection of further scan parameters may be displayed. These may include, for example, all the scan parameters that influence gradients and/or high frequency pulses, such as bandwidths, flip angles, repetition times (TR), echo times (TE), etc.

In a further act 150, similar to act 120, one or more second scan parameter values that are assigned to the one or more second scan parameters are set. In this setting, the scan parameters that were set in act 120, excluding possible exceptions such as a number of slices to be recorded, are typically no longer changeable. This data input may also be completed with a click on a Next button.

In act 300, based on the one or more first scan parameter values and/or the one or more second scan parameter values, a scan protocol is prepared. This preparation may also be carried out by the evaluation unit 27.

Based on the scan protocol, in act 310, scan data may be acquired by the imaging examination apparatus (e.g., by the magnetic resonance tomograph 10). For this purpose, the scan protocol may be transferred to the control unit 22.

Figure 3:
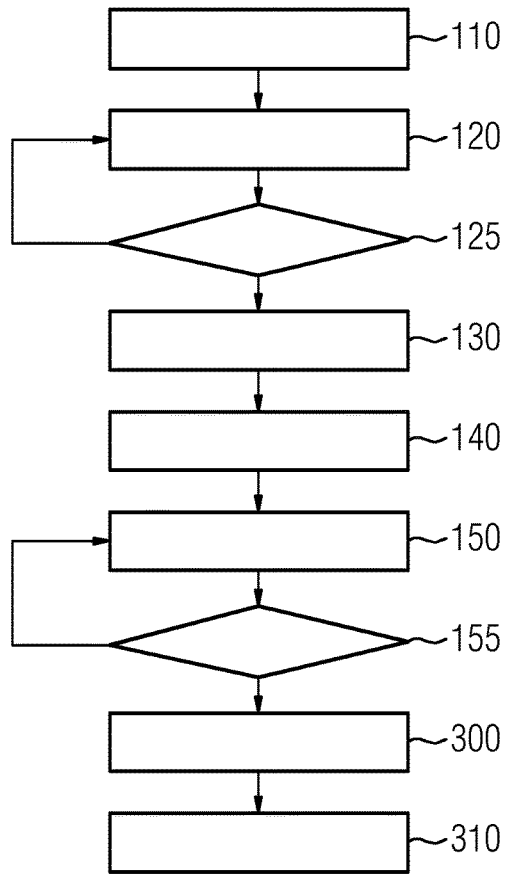
FIG. 3 is a block diagram of one embodiment of an extended method.

FIG. 3 shows an extended variant of the method. In additional monitoring acts 125 and 155, the scan parameter values set are checked for adherence to at least one boundary condition. For example, it may be checked in act 155 whether with regard to stimulation and/or heating and/or high frequency exposure of the patient 15, pre-determined limit values are adhered to. If this is not the case, the scan parameter values concerned may be changed by act 150 being repeated (e.g., on non-adherence to the at least one boundary condition, in a further act, at least one of the previously set scan parameter values may be set again). On repeated setting of previously set scan parameter values, at least one of the scan parameter values to be set again may be suggested (e.g., change suggestions for scan parameters may be offered to the operator).

Figure 4:
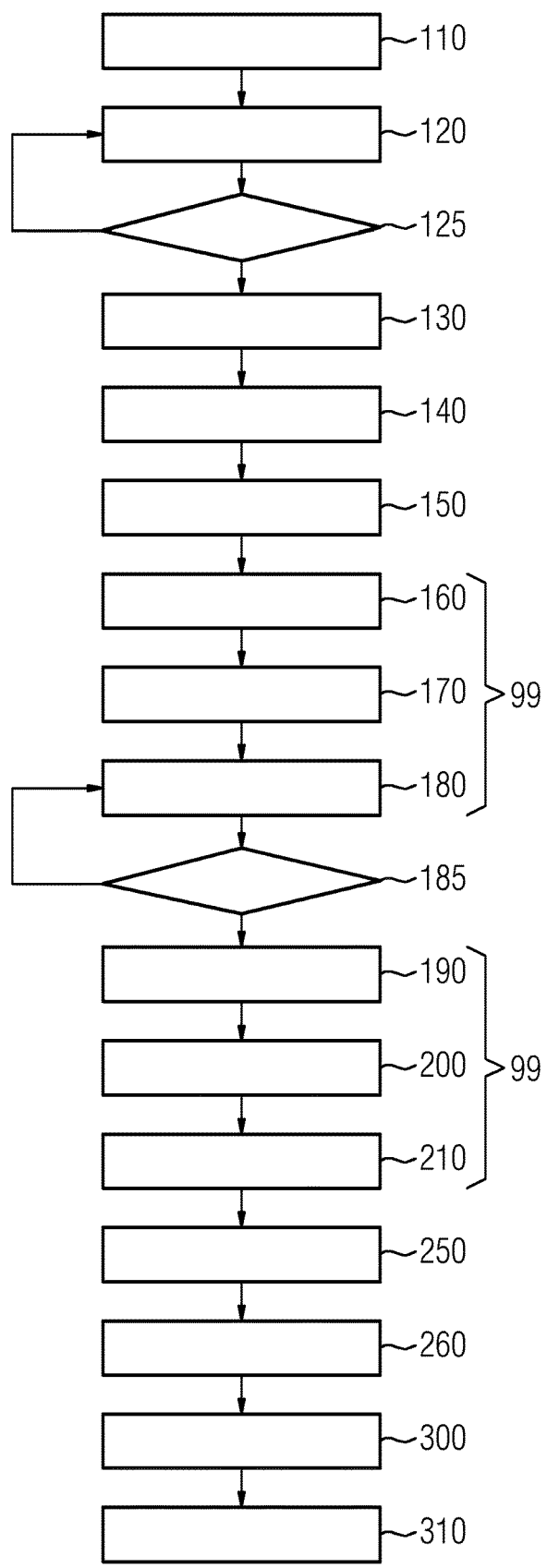
FIG. 4 is a block diagram of a further embodiment of an extended method.

That the method according to one or more of the present embodiments for the preparation of a scan protocol of a medical imaging apparatus may also include more than just two data input acts is shown in FIG. 4. The method includes additional method portions 99, where each of the one or more additional method portions includes three acts. In a respective first act 160, 190 of the method portions 99, similar to act 130, based on previously set scan parameter values that were input, for example, in the acts 120 and/or 150, a further parameter set that includes one or more further scan parameters is determined. In a respective act 170, 200 of the method portions 99, similar to the acts 110, 140, the further parameter set is provided. Thereupon, in act 180, 210 of the method portions 99, one or more further scan parameter values that are assigned to the one or more further scan parameters are set.

The exemplary embodiment shown in FIG. 4 also has monitoring acts 125, 185 in which the inputs are checked against possible presets. There are additional acts 250 and 260. In act 250, a provision of at least one postprocessing parameter takes place, and in act 260, at least one postprocessing parameter value is set, which is assigned to the at least one postprocessing parameter.

In the provision of the parameter sets in the acts 110, 140, 170, and 200, default values are proposed as scan parameter values. Using a pre-setting with default values, further setting acts may also be skipped (e.g., the preparation of the scan protocol may be concluded directly after each data input act if the operator does not wish to input further scan parameter values). For example, by clicking a Finished button in act 180, the acts 190, 200, and 210 may be skipped, and the provision of at least one parameter set may be performed in act 250.

In the provision of the parameter sets, an item of status information may also be provided, which is dependent on a number of scan parameter values to be set and/or on a number of parameter sets that include the scan parameter values that are to be set. It may thus be displayed to the operator, for example, in act 140, using a progress bar, that three data input acts 150, 180, 210, 300 are still outstanding.

Figure 5:
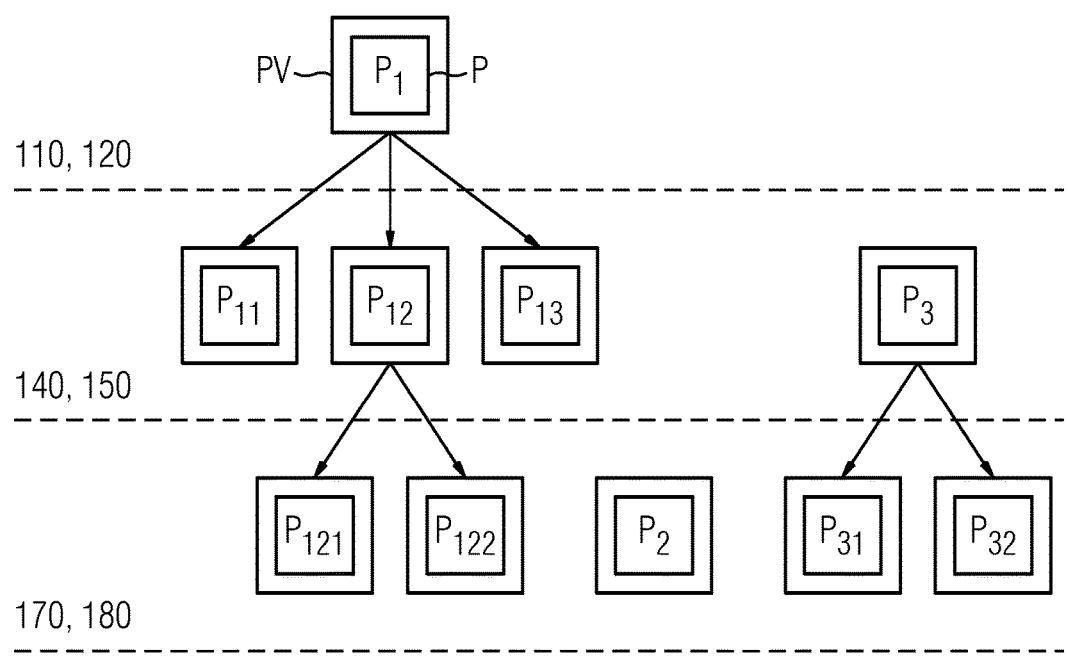
FIG. 5 is a schematic representation of scan value parameters dependent upon one another.

FIG. 5 illustrates an example in which the sequence of the parameter request is selected so that a possible parameter space is increasingly restricted step-by-step. The whole parameter space for the preparation of the scan protocol is given by the scan parameters $P_x$, where x represents a numerical index. Dependencies may exist between the scan parameters P. Thus, in the example shown, the scan parameters $P_{11}$, $P_{12}$ and $P_{13}$ depend on the scan parameter $P_1$, the scan parameters $P_{121}$ and $P_{122}$ depend on the scan parameter $P_{12}$, and the scan parameters $P_{31}$ and $P_{32}$ depend on the scan parameter $P_3$.

In a first portion that includes the acts 110 and 120, a first parameter set that in this example includes a scan parameter $P_1$ and sets associated scan parameter values PV is provided. In act 130, a further parameter set is determined. Depending on the set scan parameter value PV, for the scan parameter P1, in this example, the second parameter set provided in act 140 may include the scan parameters $P_{11}$ and/or $P_{12}$ and/or $P_{13}$ (e.g., a subset of the scan parameters $P_{11}$, $P_{12}$, and $P_{13}$; no scan parameters at all or $P_{11}$ or $P_{12}$ or $P_{13}$ or $P_{11}$ and $P_{12}$ or $P_{11}$ and $P_{13}$ or $P_{12}$ and $P_{13}$). Thus, the second parameter set includes a parameter space that is restricted by the already set one or more scan parameter values.

Likewise, restriction may be achieved by a possible selection of the scan parameter value PV belonging to the scan parameter $P_{12}$ in act 150 of the parameter space of the further parameter set provided in act 170. A similar principle applies to the scan parameter $P_3$.

On determination of a parameter set for at least one of the scan parameters of the parameter set, a permissible value range that restricts the setting of the scan parameter value of the at least one scan parameter is determined. If, for example, in act 150 a scan parameter value $PV_3$ is input for the scan parameter $P_3$, then a value range may be determined therefrom within which the scan parameter value $PV_{31}$ to be set that is assigned to the scan parameter $P_{31}$ is to lie. This value range may also be displayed on provision of the parameter set in act 170.

FIG. 5 also illustrates that the scan value parameters with the greatest influence on other scan value parameters are requested, where possible, at the beginning (e.g., these scan value parameters are included in the first parameter set, whereas scan value parameters with no influence on other scan value parameters are requested subsequently at the end). By this, the number of the necessary data input acts and/or the number of the adjustable scan parameters may be minimized so that the preparation of the scan protocol of the medical imaging apparatus may be performed quicker and easier.

The method described above in detail and the magnetic resonance tomograph disclosed are merely exemplary embodiments that may be modified by a person skilled in the art in a variety of ways without departing from the scope of the invention. The use of the indefinite article "a" or "an" does not preclude that the relevant features may also be present plurally. Similarly, the expression "unit" does not exclude the relevant components consisting of a plurality of cooperating partial components that may also be spatially distributed.

Summarizing, one or more of the present embodiments enable a method that permits a simple and intuitive preparation of a scan protocol for a medical imaging apparatus and facilitates an optimum exploitation of the efficiency of the medical imaging apparatus. In this way, scan parameter settings that previously were not selectable or only with difficulty may be performed, and a simple, guided, and intuitive setting may be enabled, where the complex relationships between scan parameters are calculated automatically from step to step without confusing the operator.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for preparation of a scan protocol of a magnetic resonance tomography apparatus, the method comprising:
   providing a first parameter set that comprises one or more first scan parameters, the one or more first scan parameters being one or more scan parameters that influence gradients, high frequency pulses, or gradients and high frequency pulses;
   setting one or more first scan parameter values that are assigned to the one or more first scan parameters;
   determining a second parameter set that comprises one or more second scan parameters dependent on the one or more first scan parameter values, the one or more first scan parameter values being different than, the one or more first scan parameters, and being one or more scan parameters that influence gradients, high frequency pulses, or gradients and high frequency pulses;
   providing the second parameter set;
   setting one or more second scan parameter values that are assigned to the one or more second scan parameters;
   determining a further parameter set that comprises one or more further scan parameters dependent on previously set scan parameter values, the one or more further scan parameters being different than the one or more second scan parameters, and being one or more scan parameters that influence gradients, high frequency pulses, or gradients and high frequency pulses;
   providing the further parameter set; and
   setting one or more further scan parameter values that are assigned to the one or more further scan parameters,
   preparing a scan protocol based on the one or more further scan parameters, and the one or more first scan parameter values, the one or more second scan parameter values, or the one or more first scan parameter values and the one or more second scan parameter values; and
   acquiring scan data by the imaging examination apparatus based on the scan protocol.

2. The method of claim 1, wherein the second parameter set comprises a parameter space that is restricted by already set one or more scan parameter values.

3. The method of claim 2, wherein setting the one or more second scan parameter values comprises setting the one or more second scan parameter values such that part of the previously set one or more scan parameter values is not changeable.

4. The method of claim 1, wherein the further parameter set comprises a parameter space that is restricted by the already set scan parameter values.

5. The method of claim 1, wherein setting the one or more further scan parameter values comprises setting the one or more further scan parameter values such that part of the previously set scan parameter values is not changeable.

6. The method of claim 1, wherein providing the first parameter set and providing the second parameter set comprises suggesting default values as scan parameter values.

7. The method of claim 1, wherein determining the second parameter set comprises determining, for at least one of the one or more second scan parameters, a permissible value range that restricts a setting of a scan parameter value of the at least one second scan parameter.

8. The method of claim 1, further comprising providing an item of status information that is dependent on a number of scan parameter values to be set, on a number of parameter sets that comprise the scan parameter values that are to be set, or on a combination thereof.

9. The method of claim 1, further comprising:
   providing at least one postprocessing parameter; and
   setting at least one postprocessing parameter value that is assigned to the at least one postprocessing parameter.

10. The method of claim 1,
    wherein the magnetic resonance tomography apparatus comprises a magnetic resonance tomograph, a computed tomography unit, an X-ray system, or any combination thereof.

11. The method of claim 1, further comprising setting, with the one or more first scan parameter values, the one or more second scan parameter values, or the one or more first scan parameter values and the one or more second scan parameter values, a slice orientation, a slice position, a slice thickness, a slice count, a slice separation, a matrix size, a field of view, a selection of acquisition coils, an echo time, a repetition time, an inversion time, a slice linkage, a bandwidth, a turbo factor, a direction of phase encoding, an averaging, or any combination thereof.

12. The method of claim 1, further comprising at least one additional monitoring, the at least one additional monitoring comprising checking the one or more first scan parameter values, the one or more second scan parameter values, or the one or more first scan parameter values and the one or more second scan parameter values for adherence to at least one boundary condition.

13. The method of claim 12, wherein the at least one boundary condition comprises a maximum stimulation, a maximum heating, a maximum high frequency exposure, or any combination thereof.

14. The method of claim 12, wherein on non-adherence to the at least one boundary condition, the method further comprises setting at least one of the previously set scan parameter values again.

15. The method of claim 14, wherein on repeated setting of previously set scan parameter values, the method further comprises suggesting at least one of the scan parameter values to be set again.

16. A magnetic resonance tomography apparatus comprising:
- a display unit configured to provide a plurality of parameter sets, each parameter set of the plurality of parameter sets comprising at least one scan parameter, the at least one scan parameter being at least one scan parameter that influences gradients, high frequency pulses, or gradients and high frequency pulses;
- an input unit configured to set scan parameter values that are assigned to the scan parameters, respectively;
- a processor configured to:
  - determine a parameter set based on at least one scan parameter value that has been set;
  - determine a further parameter set that comprises one or more further scan parameters dependent on previously set scan parameter values, the one or more further scan parameters being different than the previously set scan parameter values, and being one or more scan parameters that influence gradients, high frequency pulses, or gradients and high frequency pulses;
  - provide the further parameter set;
  - set one or more further scan parameter values that are assigned to the one or more further scan parameters; and
  - prepare a scan protocol based on the one or more further scan parameter values.

17. A computer program product comprising a non-transitory computer-readable storage medium storing a program including instructions executable by a programmable computer system of a magnetic resonance tomography apparatus to prepare a scan protocol of the magnetic resonance tomography apparatus, the instructions comprising:
- providing a first parameter set that comprises one or more first scan parameters, the one or more first scan parameters being one or more scan parameters that influence gradients, high frequency pulses, or gradients and high frequency pulses;
- setting one or more first scan parameter values that are assigned to the one or more first scan parameters;
- determining a second parameter set that comprises one or more second scan parameters dependent on the one or more first scan parameter values, the one or more second scan parameters being different than the one or more first scan parameters, and being one or more scan parameters that influence gradients, hjgh frequency pulses, or gradients and high frequency pulses;
- providing the second parameter set;
- setting one or more second scan parameter values that are assigned to the one or more second scan parameters;
- determining a further parameter set that comprises one or more further scan parameters dependent on previously set scan parameter values, the one or more further scan parameters being different than the one or more second scan parameters, and being one or more scan parameters that influence gradients, high frequency pulses, or gradients and high frequency pulses;
- providing the further parameter set;
- setting one or more further scan parameter values that are assigned to the one or more further scan parameters; and
- preparing a scan protocol based on the one or more further scan parameter values and the one or more first scan parameter values, the one or more second scan parameter values, or the one or more first scan parameter values and the one or more second scan parameter values; and
- acquiring scan data by the imaging examination apparatus based on the scan protocol.

* * * * *